United States Patent
Osterkamp

(10) Patent No.: US 7,370,532 B2
(45) Date of Patent: May 13, 2008

(54) RF COMMUNICATIONS METHOD AND SYSTEM FOR LASER ULTRASONIC TESTING

(75) Inventor: Mark Alan Osterkamp, Weatherford, TX (US)

(73) Assignee: Lockheed Martin Corporation, Bethesda, MD (US)

( * ) Notice: Subject to any disclaimer, the term of this patent is extended or adjusted under 35 U.S.C. 154(b) by 573 days.

(21) Appl. No.: 10/044,408

(22) Filed: Jan. 11, 2002

(65) Prior Publication Data

US 2003/0135285 A1    Jul. 17, 2003

(51) Int. Cl.
*G01P 3/04* (2006.01)
*H04B 7/00* (2006.01)

(52) U.S. Cl. .......... 73/510; 73/1.79; 73/584; 73/488; 455/41.2; 455/41.3

(58) Field of Classification Search .......... 455/41.2, 455/515, 517, 64, 67.11, 67.14, 68, 41.1, 455/41.3, 69.68, 70, 556.1, 557, 552.1, 11.1; 700/11; 340/825.54, 825.72, 3.1, 5.2, 416.13, 340/539.11; 356/486, 487, 601–613; 73/1.79, 73/510, 488, 584, 602

See application file for complete search history.

(56) References Cited

U.S. PATENT DOCUMENTS

| | | | |
|---|---|---|---|
| 4,633,715 A * | 1/1987 | Monchalin | 356/486 |
| 4,841,136 A | 6/1989 | Nakayama et al. | 250/231 R |
| 4,862,802 A | 9/1989 | Streifer et al. | 102/201 |
| 5,055,666 A | 10/1991 | Miyahara | 250/206.1 |
| 5,198,868 A | 3/1993 | Saito et al. | 356/142 |
| 5,237,384 A | 8/1993 | Fukunaga et al. | 356/141 |
| 5,355,609 A | 10/1994 | Schenke | 42/103 |
| 5,585,921 A * | 12/1996 | Pepper et al. | 356/487 |
| 5,604,592 A | 2/1997 | Kotidis et al. | 356/357 |
| 5,619,326 A | 4/1997 | Takamatsu et al. | 356/357 |
| 5,621,975 A | 4/1997 | Rando | 33/227 |
| 5,754,285 A | 5/1998 | Eslambolchi et al. | 356/73.1 |
| 5,801,312 A * | 9/1998 | Lorraine et al. | 73/602 |

(Continued)

FOREIGN PATENT DOCUMENTS

EP      0314177 A2    5/1989

(Continued)

*Primary Examiner*—Edward F. Urban
*Assistant Examiner*—John J. Lee
(74) *Attorney, Agent, or Firm*—Bracewell & Giuliani LLP

(57) ABSTRACT

A system including a processor, a high-energy density system linked to the processor, and a communicator linked to the processor. The communicator comprehensively integrates a plurality of hardware and software functions associated with operating the high-energy density system into a single, convenient interface. In one exemplary embodiment, the communicator comprises a wireless communicator. In operation, the communicator generates a command signal whereby the command signal is received by the processor. Accordingly, the processor controls the high-energy density system based on the command signal. In one aspect, the communicator interfaces with a security system for selectively limiting user access through a restricted system. In another aspect, the communicator is used for object information storage and retrieval associated with operating a high-energy density system, such as an ultrasonic laser system. In another aspect, the communicator is used to control a robotic device. In one exemplary embodiment, a wireless communicator continuously generates at least one command signal based on a typematic rate of interface.

13 Claims, 13 Drawing Sheets

U.S. PATENT DOCUMENTS

| | | |
|---|---|---|
| 5,883,697 A | 3/1999 | Ohyama ...................... 355/18 |
| 6,025,942 A | 2/2000 | Scifres ....................... 359/125 |
| 6,085,155 A | 7/2000 | Hayase et al. ................ 702/40 |
| 6,087,645 A | 7/2000 | Kitajima et al. ......... 250/203.1 |
| 6,094,189 A | 7/2000 | Quillen et al. .............. 345/158 |
| 6,184,979 B1 | 2/2001 | Hirano et al. ............... 356/247 |
| 6,240,312 B1 | 5/2001 | Alfano et al. ............... 600/476 |
| 6,283,756 B1 | 9/2001 | Danckwerth et al. ......... 434/11 |
| 6,327,219 B1 * | 12/2001 | Zhang et al. ................ 342/55 |
| 6,335,943 B1 | 1/2002 | Lorraine et al. .............. 372/28 |

FOREIGN PATENT DOCUMENTS

| | | |
|---|---|---|
| EP | 0486245 A1 | 5/1992 |
| EP | 0619662 A2 | 10/1994 |
| EP | 0700692 A1 | 2/1996 |
| EP | 0797074 A2 | 9/1997 |
| EP | 0939469 A2 | 9/1999 |

\* cited by examiner

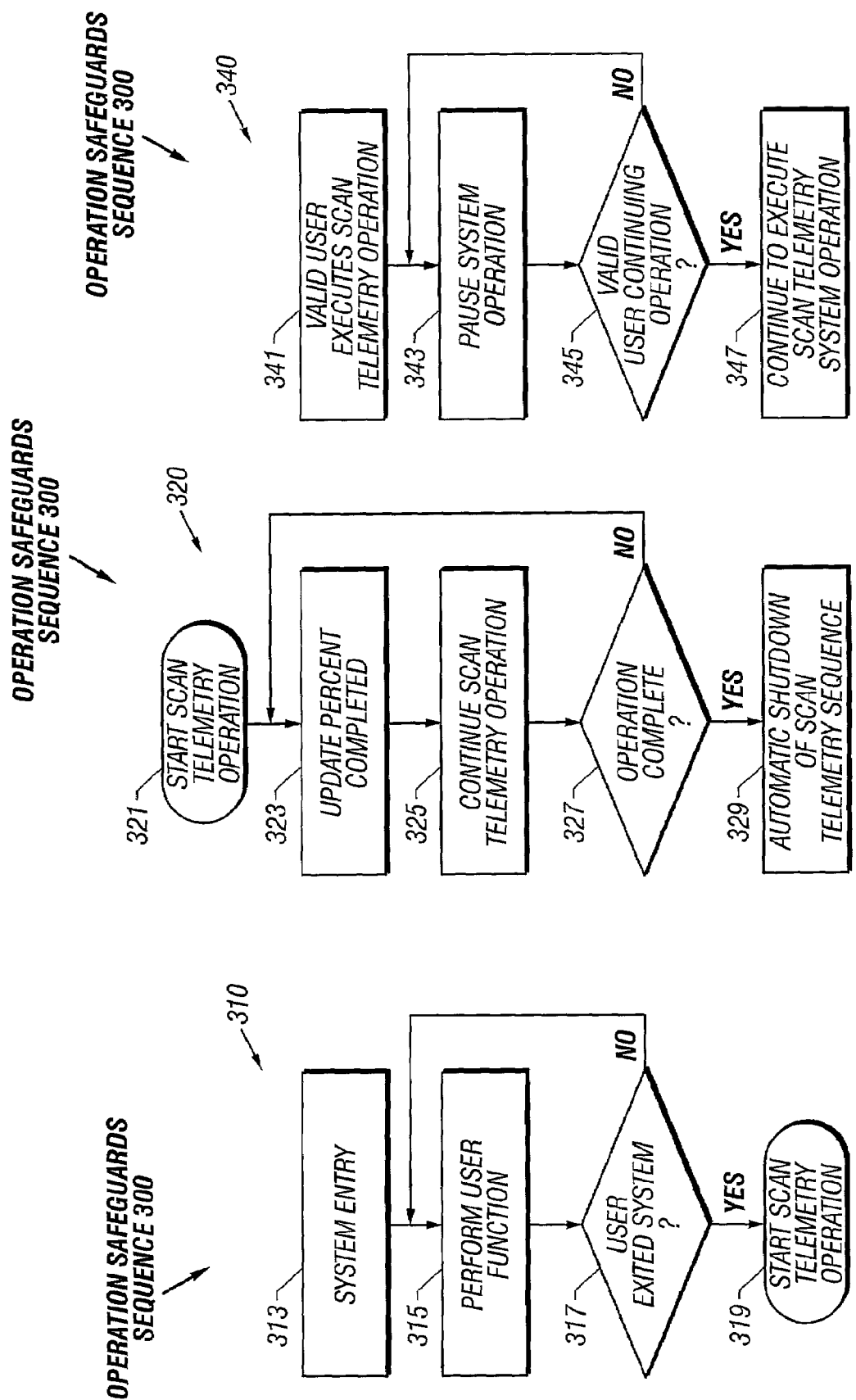

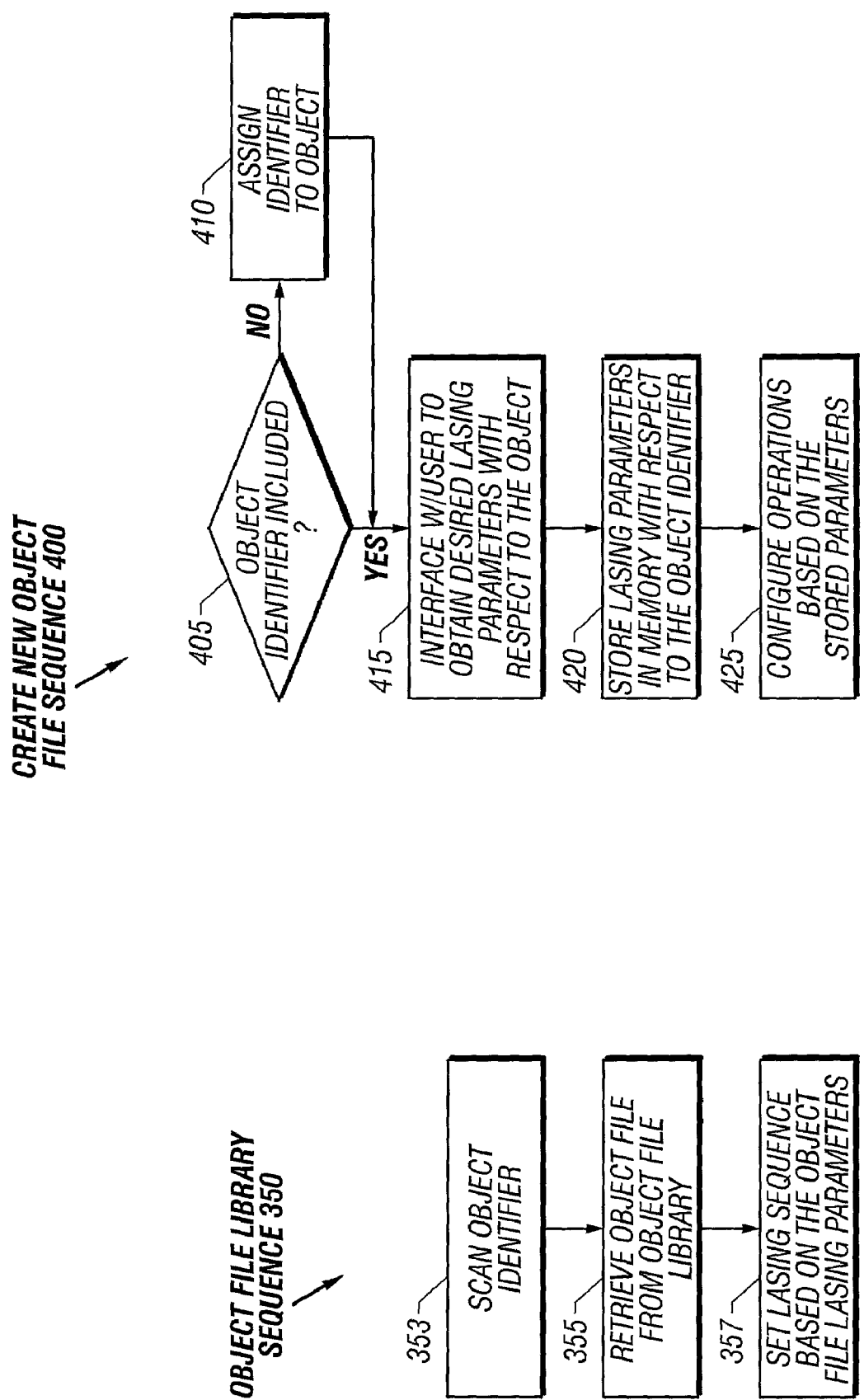

RF COMMUNICATIONS METHOD AND SYSTEM FOR LASER ULTRASONIC TESTING

BACKGROUND OF THE INVENTION

1. Field of the Invention

The present invention generally relates to a system for tracking and managing operations associated with high-energy density systems, such as for example, laser systems and electron beam systems. More particularly, the invention relates to a system and method for controlling a high-energy density system by generating and processing a command signal. More particularly, it relates to a wireless communicator for generating a command signal so as to operate the high-energy density system, such as a laser ultrasonic system among others, based on the command signal.

2. Description of the Prior Art

Many typical examples of high-energy density systems include lasing systems or particle beam systems. Often, high-energy density systems include a complex array of hardware and software networked within a designated area.

Illustratively, a high-energy laser system may include a gantry robot for accurately directing a laser beam onto a particular portion of a workpiece. Typically, a laser application head moves about a network of predefined paths on a series of gantry platforms provided by the gantry robot. The motion of the gantry robot for directing the laser head is based on instructions executed in a computer readable code by at least one processor associated with the high-energy density system.

It should be said that the processors associated with operating these high-energy density systems typically comprise a network of stationary and/or hardwired computers, including for example but not limited to microcomputers, mainframe computers, or even super computers. Although smaller, microcomputers are still difficult to move about the area defining the high-energy density system due to their large size and hardwiring configuration associated with the network for the high-energy density system. Illustratively for example, a workman wishing to confirm the current position of a laser scanning head while calibrating, the workman may be in a confined area either too small for operating a portable microcomputer or must constantly look between the computer's monitor and the position of the scanning head in a relatively cramped area.

High-energy density systems may further include other hardware components and respective operational code for facilitating operations of the high-energy density system. For example, the high-energy density system may include an optical hardware system for further directing the placement of laser energies with respect to the workpiece.

Often, a designated work area includes a barrier for enclosing the high-energy density system and protecting system from various external factors which could potentially disrupt the existing networked relationship. For example, such factors may include entry by unauthorized personnel and equipment within the designated area. Often, the network between hardware and software includes a conspicuous placement of wires, cables, and even large mainframe computers in places which may hinder the operations of a user or, potentially, injure a user. In short, the operational area defining a high-energy density system is often cluttered and hazardous. In that high-energy density systems are complex and often span a vast work area, a workman may traverse great distances between the workpiece and the associated hardware or desired computer to perform various operations, such as for example adjusting to position of the laser scanner head relative to the workpiece or shutting down the high-energy density system for maintenance and repair purposes.

Inasmuch, there currently does not exist an interface that is safe, portable, easy to use, and easy to handle so as to comprehensively control operations associated with a high-energy density system by interacting with the network hardware and software components. Many other problems and disadvantages of the prior art will become apparent to one skilled in the art after comparing such prior art with the present invention as described herein.

SUMMARY OF THE INVENTION

Aspects of the invention are found in a system and method for controlling high-energy operations via a communicator. In particular, the system includes a processor and a high-energy density system linked to the processor. Illustratively, for example, the high-energy density system may include among others a laser ultrasonic system, an apparatus for generating and detecting ultrasonic surface displacements on a remote object, a laser system, a particle beam system, and an electron beam system, among others. The system further includes a communicator. The communicator comprehensively integrates a plurality of hardware and software functions into a simple interface. Moreover, the communicator is portable, handheld, easy to use, and safe in that it does not add to space limitations associated with a high-energy density system and can be operated in tight spaces. In one exemplary embodiment, the communicator comprises a wireless communicator.

In operation, the communicator generates a command signal whereby the command signal is received by the processor. The processor then controls the high-energy density system based on the command signal. As such, operation of the high-energy density system is based on the command signal.

The communicator includes an interface for receiving user input so as to comprehensively access various functions associated with the high-energy density system. In one aspect, for purposes of security or, commonly, "user validation", the communicator interfaces with a security system for selectively limiting user access through a restricted system. The security system includes an identifier associated with a particular user. Illustratively, for example, an identifier may include a bar code incorporated within a security badge for the particular user. On accessing the identifier, the communicator potentially generates a valid user command signal based on the identifier based on the valid user command signal. A processor associated with the communicator thus provides user entry through at least one barrier provided by the restricted system.

In another aspect, the communicator is used for object information storage and retrieval. High-energy density systems, such as ultrasonic laser systems, use energy such as laser energy to determine the physical parameters of an associated object, such as for example, among others, an object may include an aircraft wing subject to defect inspection. In particular, the communicator interfaces with a system for processing information. In one exemplary embodiment, the system includes an identifier associated with the object. The communicator reads the identifier and generates a command signal based on the identifier. Therefore, the command signal enables the high-energy density system to recognize and configure operations to accommodate the object associated with that identifier.

In another aspect, the communicator is used to control a robotic device. Typically, high-energy density systems include robotic devices for positioning the high-energy density system with respect to the object, such as a laser application head for example. In one exemplary embodiment, the communicator comprises a wireless communicator for generating a command signal. A processor associated with the wireless communicator receives the command signal and operates the robotic device based on the command signal. In one exemplary embodiment, the communicator continuously generates at least one command signal. In yet another exemplary embodiment, the communicator continuously generates at least one command signal based on a typematic rate of interface.

Other aspects, advantages, and novel features of the present invention will become apparent from the detailed description of the invention when considered in conjunction with the accompanying drawings.

BRIEF DESCRIPTION OF THE DRAWINGS

The present invention is illustrated by way of example and not limitation in the accompanying figures, in which like references indicate similar elements, and in which:

FIG. 10 is a flow diagram illustrating one embodiment of an operation safeguard sequence accessed through the validation menu of FIG. 6, the embodiment including a single user routine of FIG. 10a, a single operational routine of FIG. 10b, and operations pause routine of FIG. 10c;

FIG. 11 is a flow diagram illustrating one embodiment of an object file library sequence accessed through the object identification menu of FIG. 7;

FIG. 12 is a flow diagram illustrating one embodiment of a create new object file sequence accessed through the object identification menu of FIG. 7;

Figure 1:
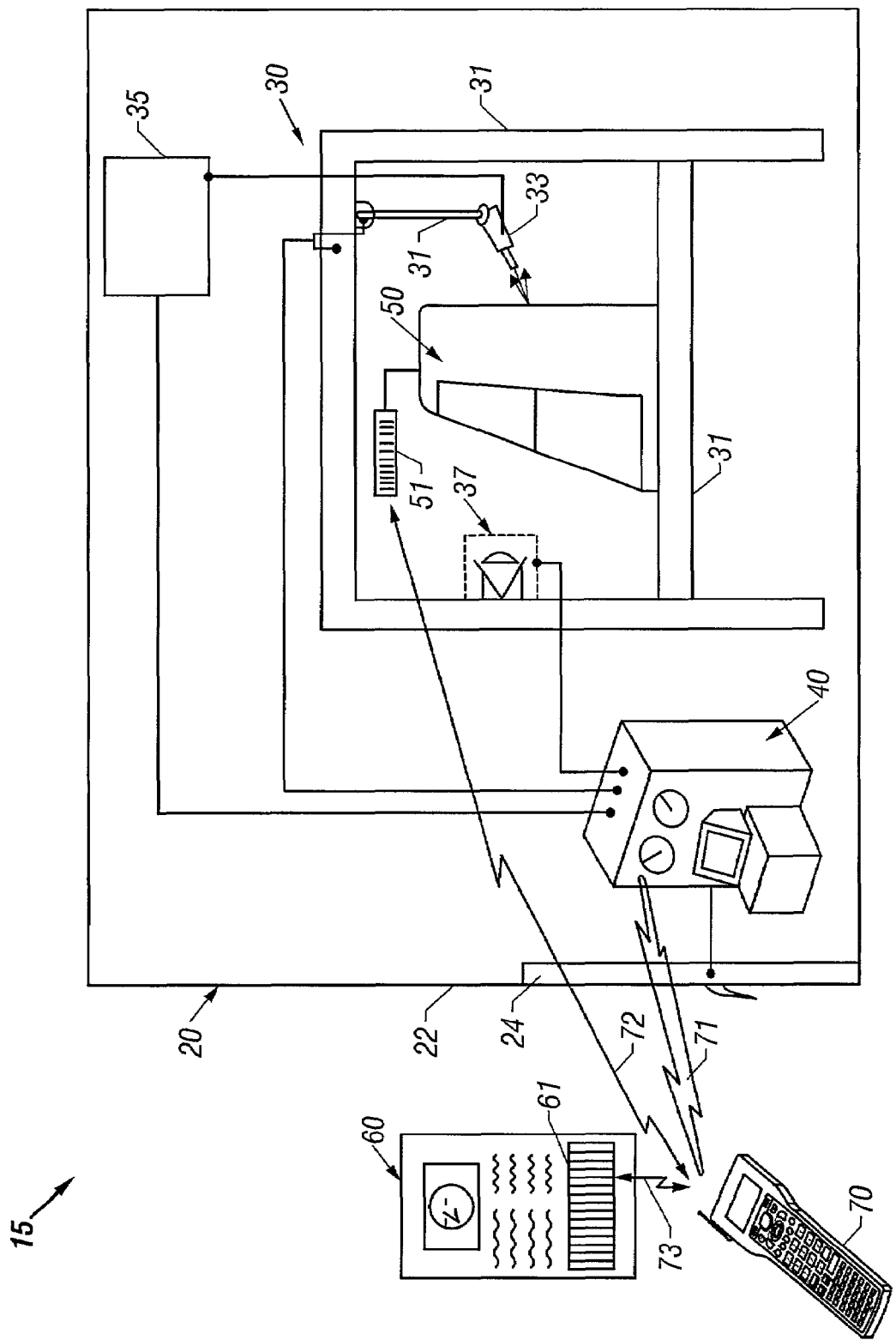
FIG. 1 is a schematic diagram illustrating a system for controlling high-energy operations according to the present invention featuring a communicator in operational engagement with a high-energy density system.

Skilled artisans appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF THE PREFERRED EMBODIMENT

For a more complete understanding of the present invention and the advantages thereof, reference is now made to the following description taken in conjunction with the accompanying drawings in which like reference numerals indicate like features and wherein:

FIG. 1 is a schematic diagram of a system for controlling high-energy operations in an exemplary aspect of the invention. In general, the system 15 includes a processor 40, a high-energy density system 20 linked with the processor 40, and a communicator 70. In operation, the communicator 70 generates a command signal 71 so that the processor 40 receives the command signal 71 and, thus, operates the high-energy density system 20 based on the command signal 71.

For the exemplary embodiment of FIG. 1, the high-energy density system 20 comprises an apparatus for detecting ultrasonic surface displacements on a remote target, such as for example a laser ultrasonic system. In one exemplary embodiment, the high energy density system 20 comprises an apparatus for generating ultrasonic surface displacements on a remote target, such as for example a laser ultrasonic system. In one exemplary embodiment the high energy density system 20 comprises a laising system. Those of ordinary skill in the art, however, should readily recognize that the high-energy density system 20 may comprise other systems of a type well known in the industry such as, for example, particle beam systems, electron beam systems, or other high-energy density emitting systems.

Accordingly, for the exemplary embodiment of FIG. 1, the high-energy density system 20 includes a robotic device 30 for moving a laser application head 33 to a desired portion of an object 50. Illustratively, in operation, the laser application head 30 is moved to a desired portion of the object 50 so as to generate a laser signal that causes the object 50 to vibrate. In part, the Doppler shift from the laser signal reflected off of the object 50 is received by the high-energy density system 20 and processed so as to detect physical characteristics associated with the object, such as cracks, defects in the interior of the composite material defining the object 50 or irregularities in dimensioning and tolerancing the object.

Figure 2:
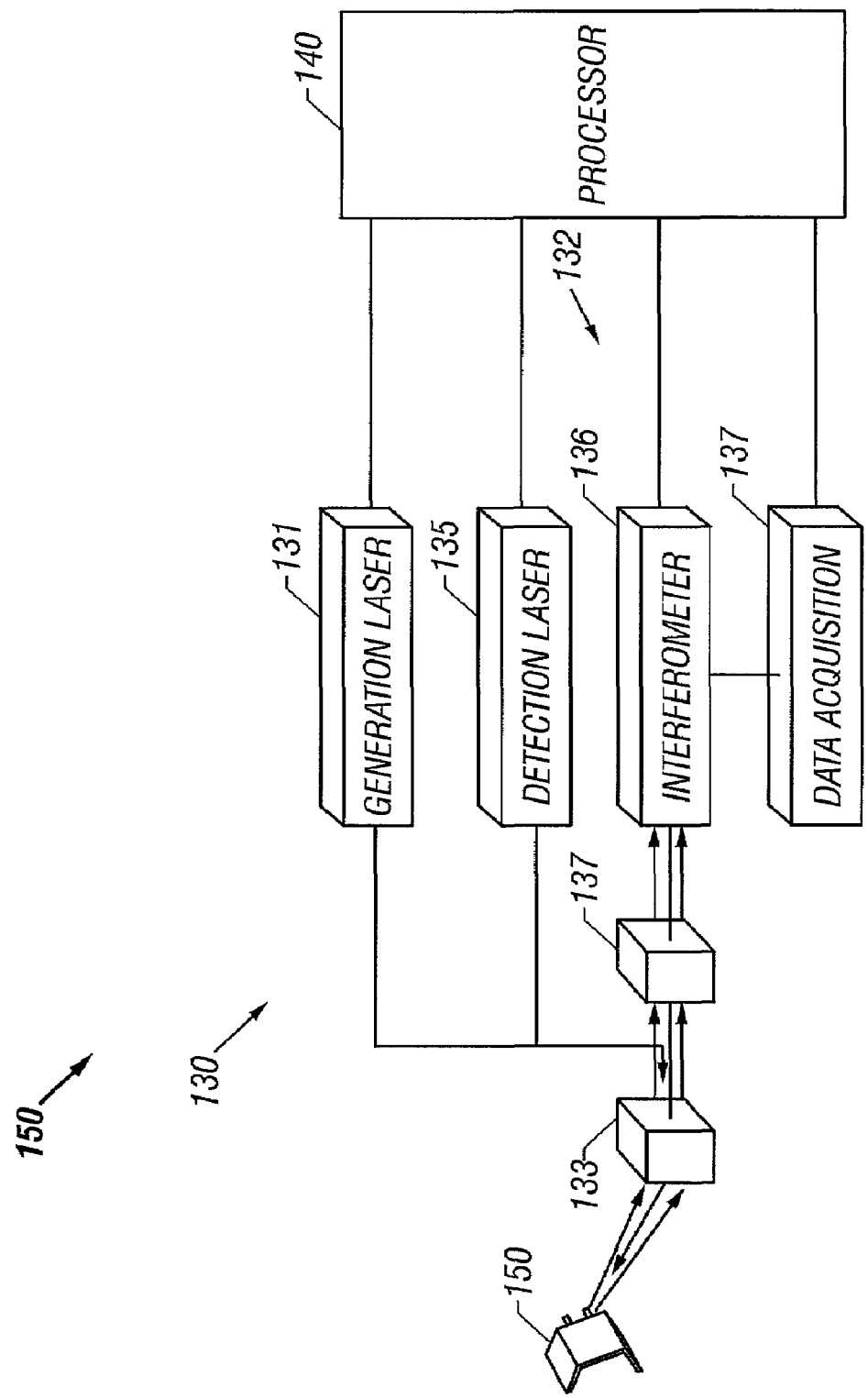
FIG. 2 illustrates various hardware aspects associated with the high-energy density system of FIG. 1.

FIG. 2 shows a detailed schematic diagram of the laser ultrasonic system 150 that defines the high-energy density system 20 for the exemplary embodiment of FIG. 1. It should also be said that in FIG. 1, the laser generation and detection arrangement is schematically shown by reference numeral 35. The laser ultrasonic system 150 includes a laser detection and generation arrangement 130 coupled to a processor 140. Ultimately, the laser detection and generating arrangement 130 identifies characteristics associated with the object 150.

Specifically, in operation, a laser beam is emitted from a generation laser 131 through a scanner 133 onto the object 150. For the embodiment of FIG. 2, the scanner 133 includes a scanning head. Initially, the scanning head identifies dimensions and material characteristics of the object among other aspects. Based on the identified characteristics, the generation laser 131 directs a laser generation signal onto the object 150. The laser beam from the generation signal then vibrates the object 150.

The laser generation and detection arrangement 130 further includes a laser detection unit 132. Shown in FIG. 2, the laser detection unit 132 includes a detection laser 135. As the generation laser 131 effectively vibrates the object 150, the detection laser 135 sends a detection laser signal through the scanner 133 onto the object 150. On reflectively returning to the scanner 133, the returning laser signal having a Doppler shift induced by the vibrating object 150 is collected by the scanner 133 and ultimately sent to an interferometer 136. The interferometer 136 collects the returning detection laser signal. A data acquisition unit 138, coupled to the interferometer 136, converts the detection laser signal into a voltage signal. A processor 140 then receives the voltage signal and processes the information associated with the signal. It should be added that to ensure optimal reception by the interferometer 136 in a bandwidth of interest, the exemplary embodiment of 132 further includes an optical array 137 positioned along the return path of the detection laser signal between the scanner 133 and the interferometer 136.

Referring to FIG. 1, the robotic device 130 includes a gantry assembly 31. The gantry assembly 31 features a network of pathways so that the laser application head 33 traverses about these pathways so as to obtain a position with respect to the object 150. Moreover, for the embodiment of FIG. 1, the high-energy density system includes an optical array 37 for further directing a laser emission with respect to the object 50.

For the embodiment of FIG. 1, the communicator 70 is provided to facilitate operation of the high-energy density system 20 via interfacing with the processor 40. For the exemplary embodiment of FIG. 1, the processor 40 includes an array of networked devices and program sequences for operation based on instructions in a computer readable code. Accordingly, the processor 40 receives and processes the signal from the communicator 70 as well as operates the high-energy density system based on the command signal generated by the communicator. However, in another exemplary embodiment, the processor 40 may receive the command signal from the communicator only so that at least one other processor apart from the processor 40 operates aspects of the high-energy density system 20.

Figure 3:
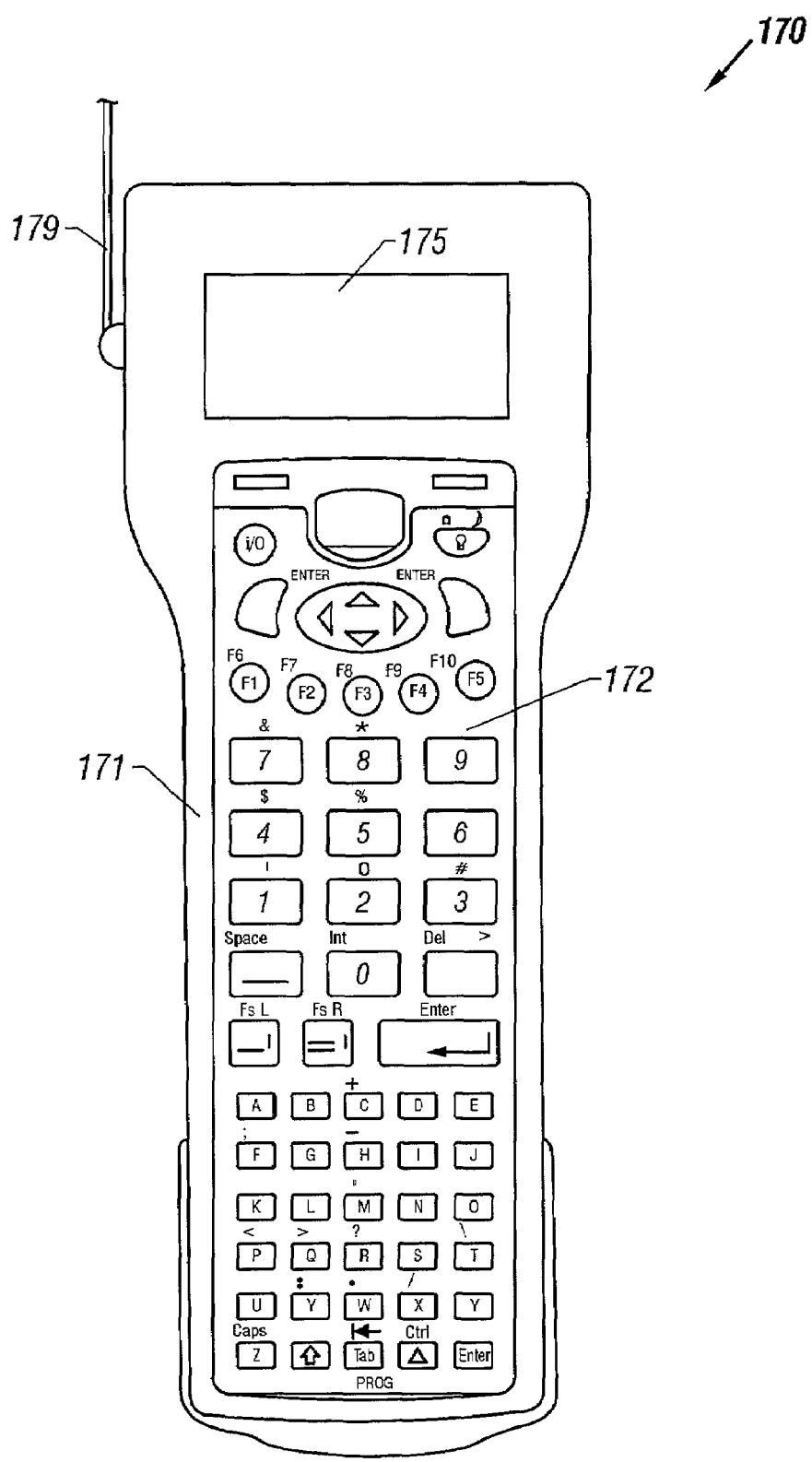
FIG. 3 is a top plan view illustrating various aspects of the communicator of FIG. 1.

Referring to FIG. 3, a communicator 170 is shown. The communicator 170 includes a body 171. In one exemplary embodiment, as shown in FIG. 3, the body 171 is configured to be received by one hand of a user to thus afford the aspects, among others, of portability, ease of use, and the ability to be used in places having limited capacity for space. The communicator 170 includes an interface 172 for receiving commands from the user so as to ultimately generate a command signal based on the users. As shown in FIG. 3, the interface 172 comprises a touch key interface including alpha numeric as well as cursor direction indicia to further assist the user in interfacing with the communicator 170. Those of ordinary skill in the art will readily recognize other interfaces such as for example voice activated or activation via the electromagnetic spectrum.

The communicator 170 includes a display 175. The display 175 enables the communicator 170 to interface with a user. For the exemplary embodiment of FIG. 3, the communicator 170 includes a wireless assembly 179 for transmission of information between the communicator 170 and the processor 40 including the command signal generated by the communicator 170. In the exemplary embodiment of FIG. 3, the wireless assembly 179 comprises a radio frequency (RF) based communication system of a type well known in the industry, but in other embodiments include communication systems of a type well known in the industry such as for example, microwave based communication systems or infrared based communication systems.

Figure 4:
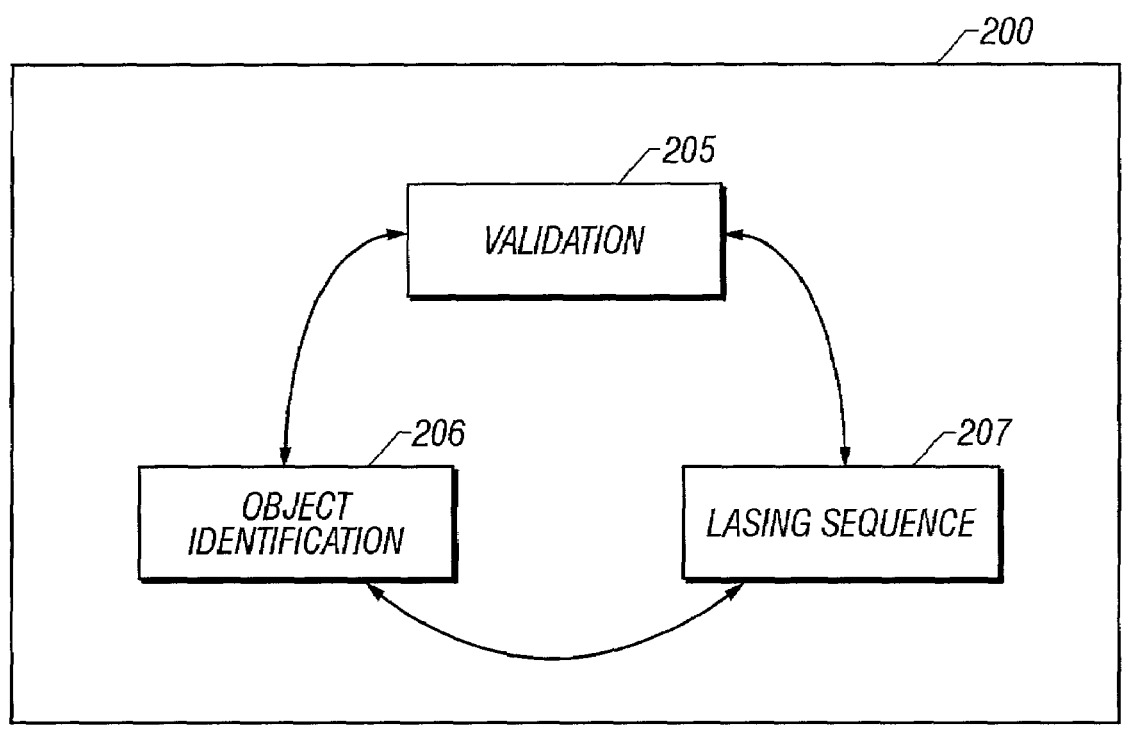
FIG. 4 is a schematic diagram showing one exemplary embodiment of a communicator operation menu implemented by a communicator of a high-energy density system.

For the embodiment of FIG. 4, a communicator operation menu 200 is shown. In particular, in one exemplary embodiment, the communicator operation menu 200 is indicated on the display of 175 of the communicator 170. In effect, the communicator operation menu 200 provides a main menu to the user of the communicator 170 for directing the user to areas function to be performed by the communicator 170.

In particular, the communicator operation menu 200 includes among others a validation directory field 205, an object identification directory field 206, and a lasing sequence directory field 207. The validation directory field 205 is associated with a security system for restricting access through the barrier 22. The object identification directory field 206 is associated with recognizing the size and composition of a particular object for use by the high-energy density system. In addition, the lasing sequence directory field 207 is associated with laser generation and detection of the object 170.

Figure 5:
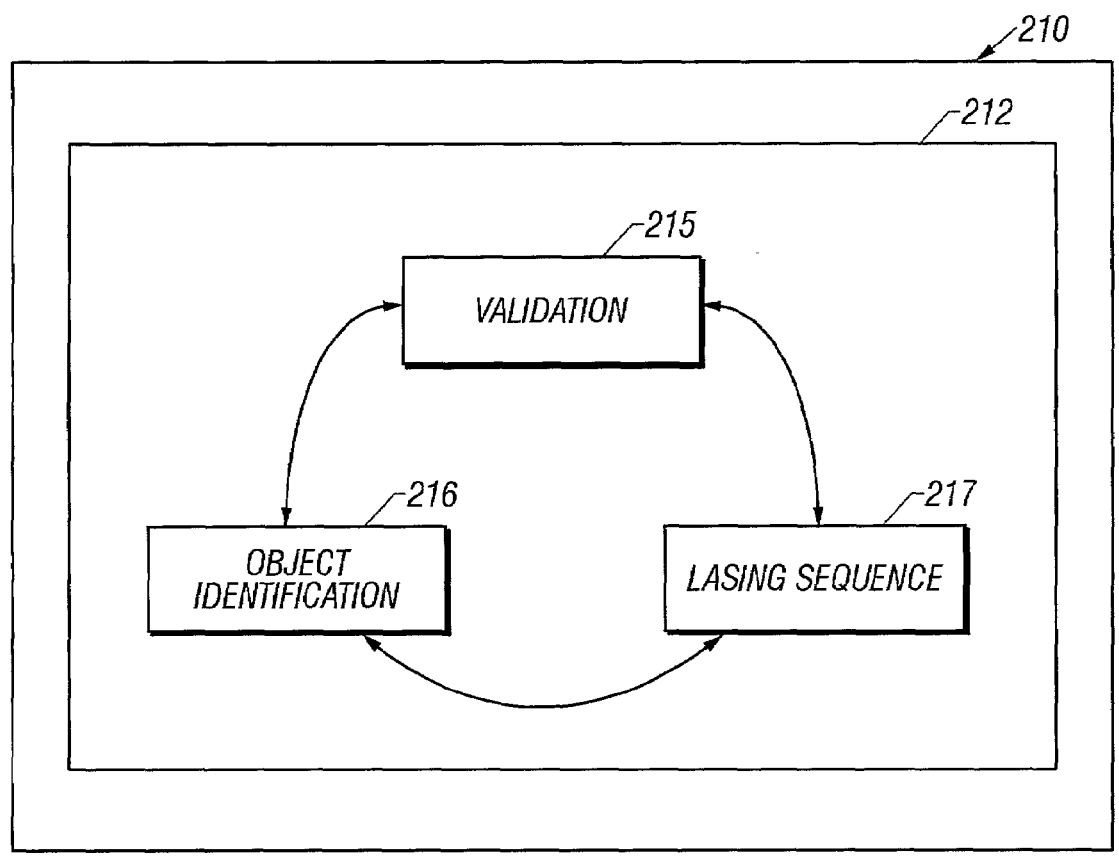
FIG. 5 is a schematic diagram showing another embodiment of a communicator operation menu implemented by a communicator.

In the embodiment of FIG. 5, a main communicator operation menu 210 provides a communicator operation menu sequence 212 comprises a subdirectory field. As shown in FIG. 5, the communicator operation menu sequence 212 includes a validation directory field 215, an object identification directory field 216, and a lasing sequence directory field 217 among others.

Figure 6:
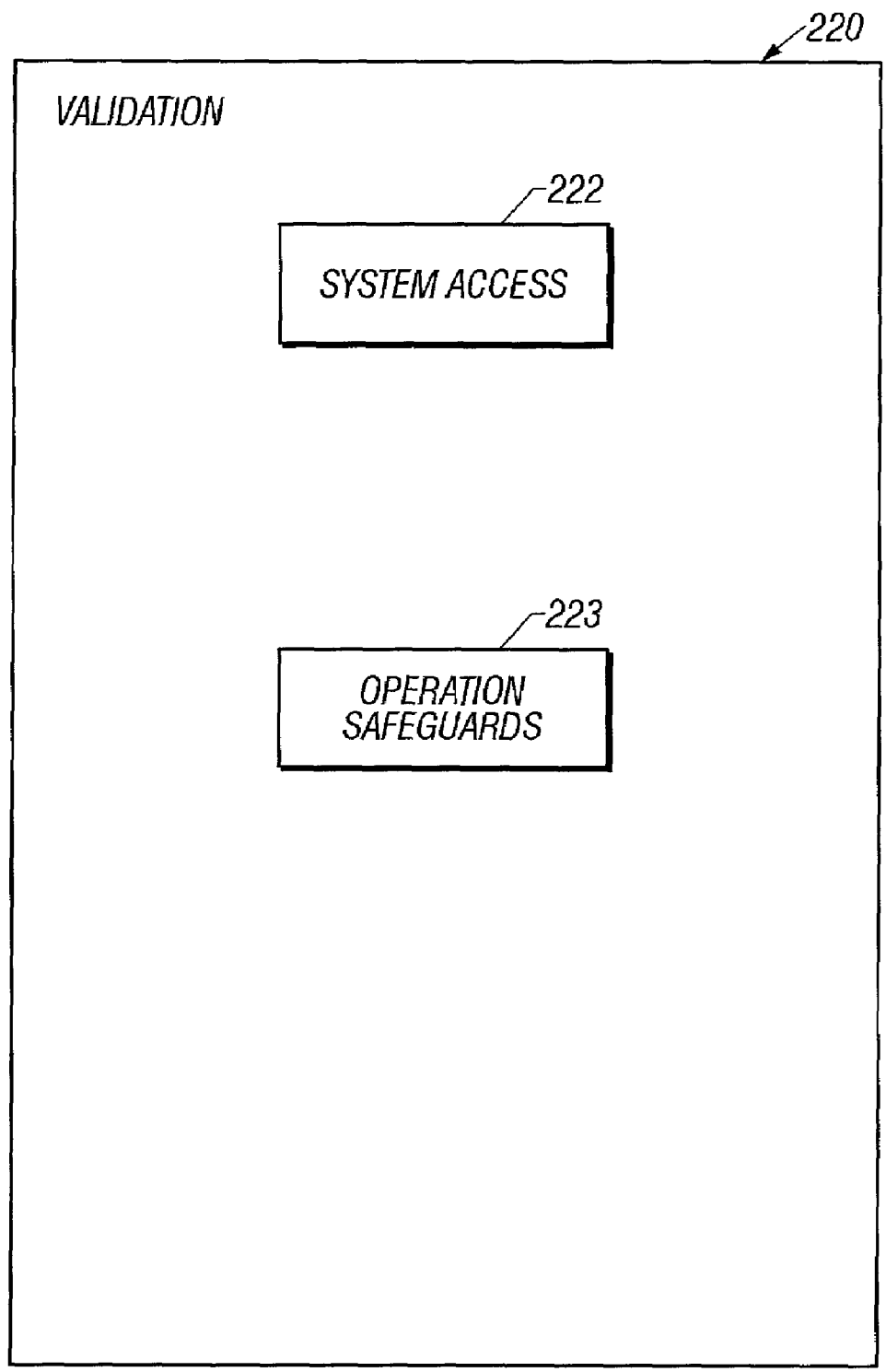
FIG. 6 shows one embodiment of a validation menu implemented by a communicator.

In FIG. 6, a validation menu 220 is provided in one exemplary embodiment as a subdirectory menu for the validation directory field 205 of FIG. 4. The validation menu 220 includes a system access directory field 222 and an operation safeguards directory field 223 among others.

Figure 7:
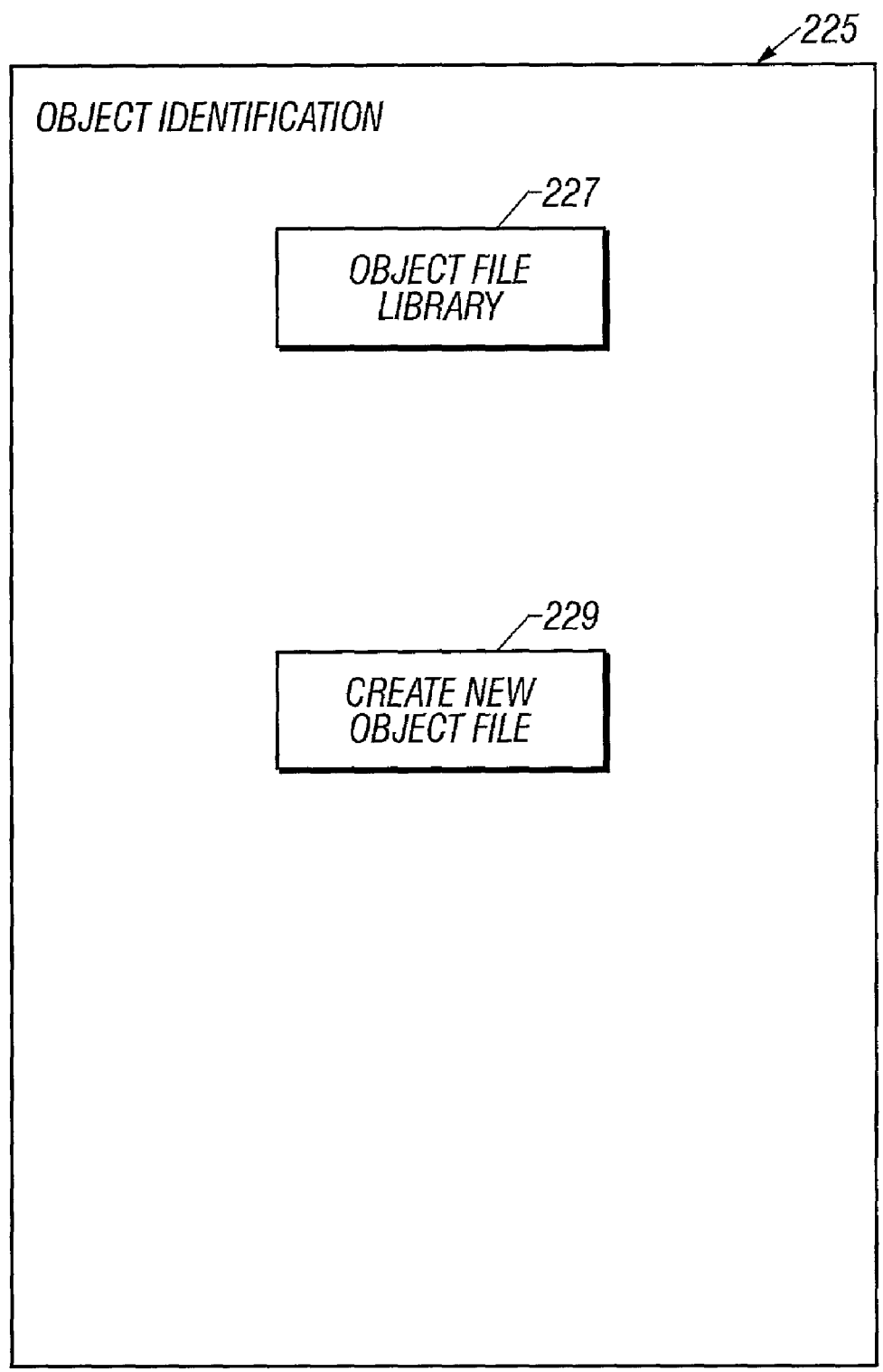
FIG. 7 illustrates one embodiment of an object identification menu implemented by a communicator.

FIG. 7 shows an object identification menu 225 provided in one exemplary embodiment as a subdirectory menu for the object identification directory field 206 of FIG. 4. The object identification menu 225 includes an object file library directory field 227 and a create a new object file directory field 229 among others.

Figure 8:
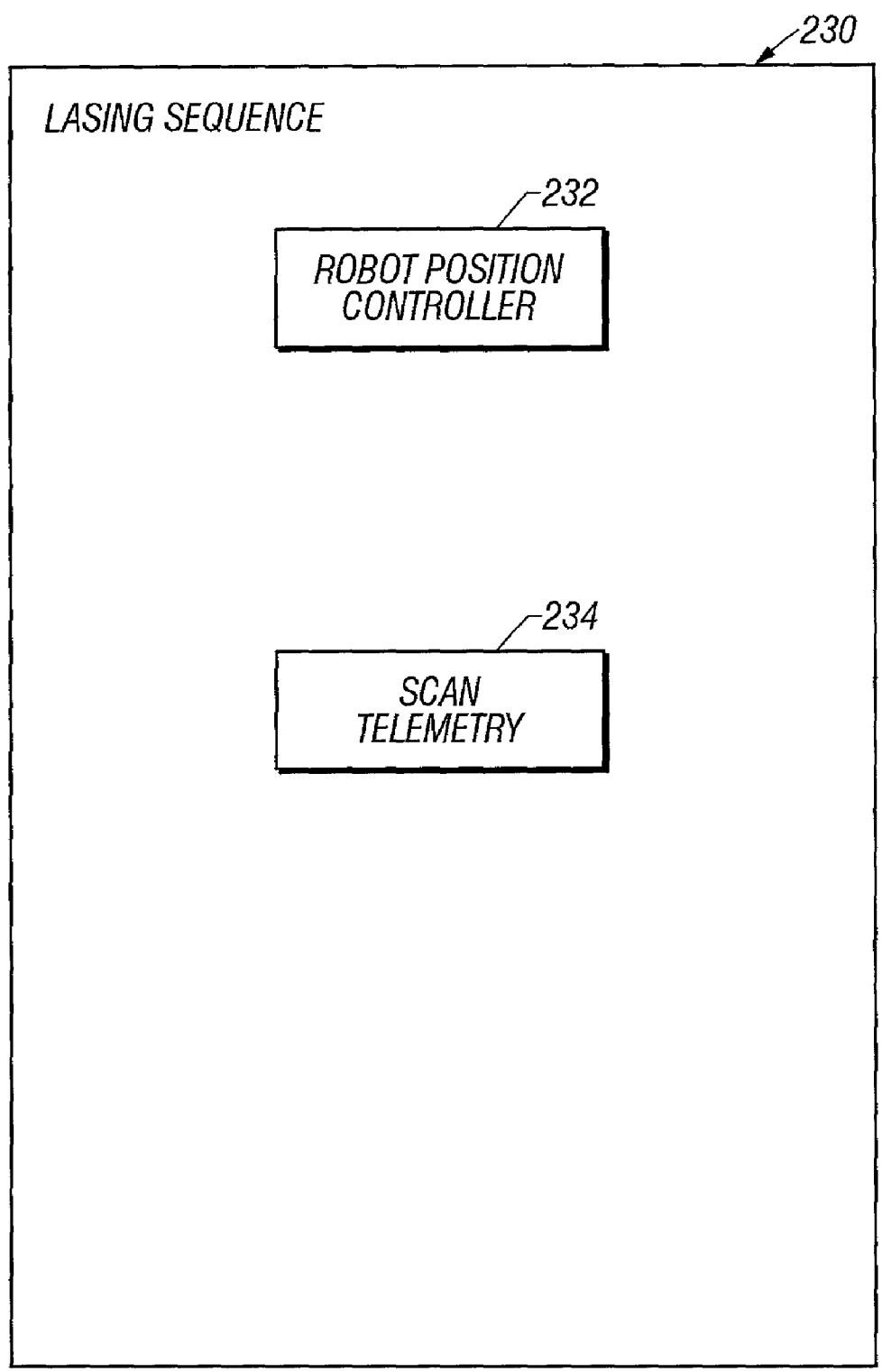
FIG. 8 illustrates a lasing sequence menu implemented by a communicator.

In FIG. 8, a lasing sequence menu 230 is provided in one exemplary embodiment as a subdirectory menu for the lasing sequence directory field 207 of FIG. 4. The lasing sequence menu 230 includes a robot position controller directory field 232 and a scanned telemetry directory field 234 among others.

Figure 9:
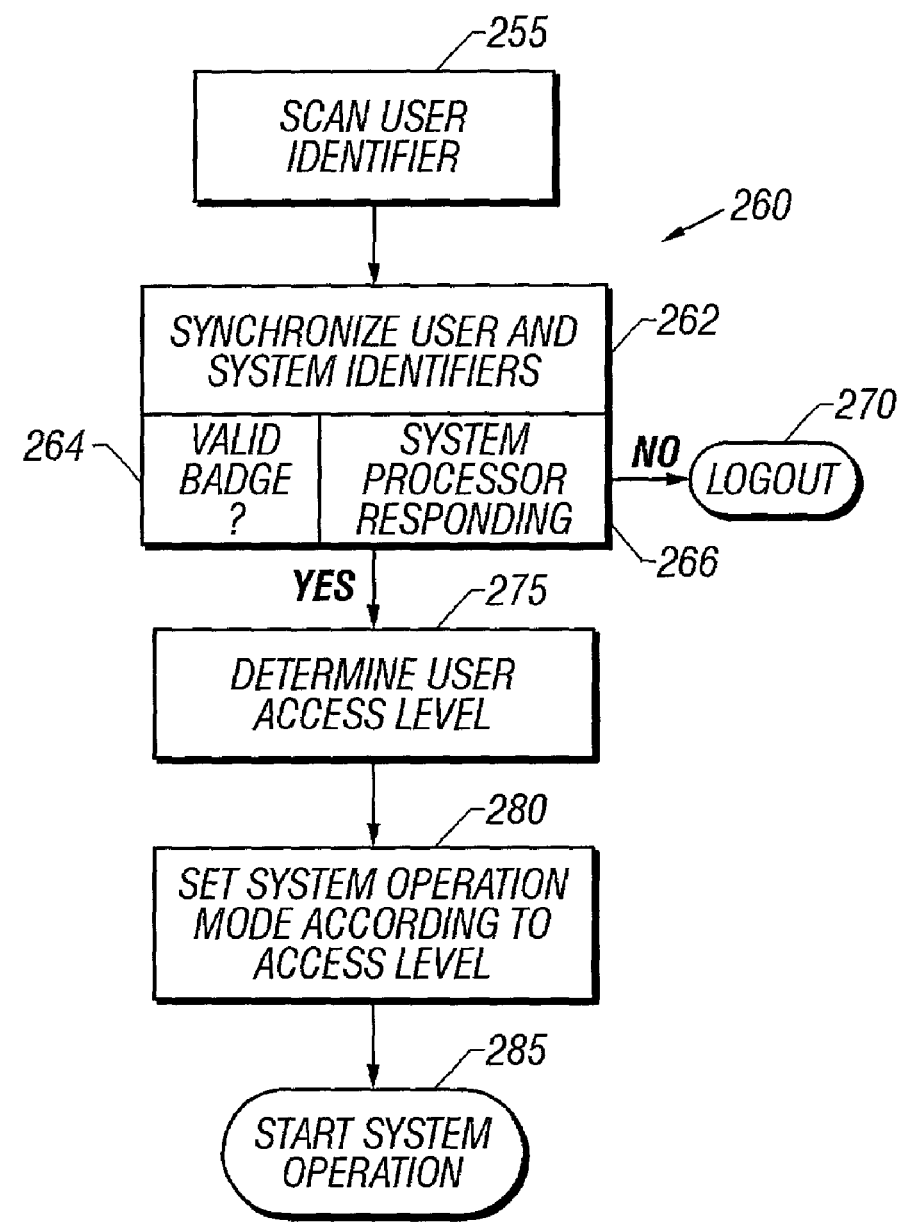
FIG. 9 is a schematic diagram illustrating one embodiment of a system access sequence accessed through the validation menu of FIG. 6.

Referring now to the particular operational sequences, FIG. 9 shows one exemplary embodiment of a system access sequence 250 executed by interfacing with the system access directory field 222 provided by the communicator 170. As shown in FIG. 1, the system 15 includes a security system for selectively limiting user access to a restricted system.

In particular, the security system includes the barrier 22 for enclosing a restricted system. In one exemplary embodiment, the restricted system includes the high-energy density system 20. In one exemplary embodiment, the restricted system includes a lasing system. The security system includes the communicator 70 coupled to the processor 40. The security system further includes an identifier 61 associated with the user. As shown in the exemplary embodiment of FIG. 1, the identifier 61 is incorporated with a security badge 60 for a respective user. In one exemplary embodiment, the identifier 61 includes barcode indicia for interfacing with the communicator 70. Those of ordinary skill in the art will recognize other suitable means for identifying a user such as for example prerecorded media, biological-interfacing elements such as retinal or skin tissue scans, among others.

The communicator 70 then scans the identifier 61 and, after determining whether a user is a valid user, generates a command signal based on the identifier 61 as depicted by reference arrow 73. In addition, the processor 40 independently includes access data associated with the specified identifier. As such, the processor 40 provides user entry through the barrier 22 via a passageway 24 based on the valid user command signal and by comparison with access data associated with the user's particular identifier prestored within the processor 40.

In one exemplary embodiment, the communicator 70 selectively generates a valid user command signal based on the identifier 61. Illustratively, a user having a designated low-level identifier allows a communicator to generate a command signal for access through a predetermined number of passageways or areas within the restricted system. In one exemplary embodiment, the barrier 22 comprises at least one software control algorithm in a computer readable code that restricts operations associated with the restricted system. In one exemplary embodiment, the barrier 22 comprises at least one locked passageway associated with the restricted system.

In one exemplary embodiment, the processor 40 selectively provides user entry through the barrier 22 based on the valid user command signal and access data associated with the processor 40. Illustratively, based on the valid user command signal, the processor 40 may restrict entry through the barrier and/or various sections of the restricted system.

Referring to the system access sequence 250 of FIG. 9, the user identifier 61 is scanned by the communicator 70 in step 255. In general, for step 260, the communicator 70 determines whether the user identifier 61 is a valid user identifier with respect to the restricted system. In particular, in step 262, the communicator 70 accesses the user identifier 61 and system identifier associated with that user prestored within the processor 40. In step 264, the communicator 70 determines whether the user identifier 61 corresponds with the system identifier. In one exemplary embodiment, as an added security measure, the processor 40 and the communicator 70 in step 266 perform a real-time check to determine whether the restricted system can accommodate the user at that particular time. Accordingly, as provided by the system log-out in step 270, the communicator 70 will not provide user access at that particular time based on the real-time check. Alternatively, for a valid user identifier, the communicator 70 in step 275 determines the level of access associated with the user for the user identifier 61. Illustratively, in one exemplary embodiment, the communicator 70 may restrict access at a low level for maintenance and cleaning personnel for entry within the restricted system and afford greater access to high-level personnel such as those operating the high-energy density system for obtaining data from the object 70.

In step 280, the communicator 70 sets its system operation mode according to the access level determined in step 275. Illustratively, a user with high-level access would encounter a greater variety of directory fields displayed for access through the communicator 70 than a user with a low level access. In step 285, the communicator 70 starts system operational mode so as to operatively interface with the user and the restricted system.

FIG. 10 shows one exemplary embodiment of an operation safeguards sequence 300 as accessed by the operation safeguards directory field 223 of FIG. 6. In particular, the operation safeguards sequence 300 includes a user-restricted routine 310 of FIG. 10a. Generally, the user restricted routine 310 ensures that personnel are restricted from accessing designated areas of the high-energy density system as the high-energy density system 20 is in use. Illustratively, the user restricted routine 310 be ensure that all users have exited the restricted system prior to beginning an ultrasonic laser scanning operation.

Accordingly, in step 313, a user enters within the restricted system. In step 315 the user performs a function within the restricted system. For example, the user may enter the restricted system for maintenance or cleaning purposes, for accessing the object prior to high-energy operations, and among other reasons. In step 317, the communicator 70 engages with the processor 40 to determine whether the user has exited the restricted system. If the user has not exited the system the user restricted routine 310 loops back to step 315 so that the communicator 70 continues to be on stand-by mode prior to operation of the high-energy density system. Alternatively, once the communicator 70 determines that the user has exited the system, the communicator will then advance to display those directory fields associated with operating the high-energy density system 20.

The operation safeguards sequence 300 includes a single operation routine 320. In general, the single operation routine 320 allows for one user to access the high-energy density system at a time and complete operation before another user is allowed access and use. In this manner, the single operation system prevents confusion between the operating user and other potential users. The single operation routine 320 further prevents the possibility of subjecting equipment and personnel to hazardous conditions. Illustratively, for example if several users were using the high-energy density system at a given time, the system would dangerously fluctuate in power out-put so as to create a hazard. As another example, a hazardous condition exists by starting or operating a high-energy density system without the knowledge that another user is close enough to the high-energy density system to become injured.

As shown in FIG. 10b, operation of the high-energy density system 20 commences in step 321. Optionally through the display 175 for the communicator 170, in step 323, the user is provided an updated percentage of completion for that particular high-energy density system operation project. In step 325, the communicator 70 and the processor 40 ensure that the high-energy operation continues. In step 327, the communicator 70 and processor 40 determine whether the operation is completed. If the operation is incomplete, the single operation routine 320 is directed from step 327 back through step 323 to continue operations and, optionally, updating. If the operation is complete, the single operation routine 320 advances from step 327 to step 329. On completion, the communicator 70 and the processor 40 ensure that the high-energy density system is shut down prior to another use.

FIG. 10c shows an operations pause routine 340. In general, the operations pause routine 340 is implemented by the communicator 70 to ensure that only one user has access to the high-energy density system at a given time. Thus, should a user require the high-energy density system to pause an operation, only that user can reactivate the high-energy density system to complete their operation prior to other subsequent users.

In particular, a user starts operation of the high-energy density system 20 in step 341. In step 343, the user interfaces with the communicator 70 to pause operation of the high-energy density system. In step 345, the communicator 70 and processor 40 determine whether the pausing user wishes to resume operation of the high-energy density system from a pause mode. The operations pause routine 340 will move from step 345 back to the pause mode in step 343 until that valid user can confirm resuming operation of the high-energy density system via the communicator 70. Alternatively, if the communicator 70 and processor 40 determine that the valid user wishes to continue operation, the operations pause routine 340 advances from step 345 to step 347. In step 347, the high-energy density system continues to resume operation for that valid user.

FIG. 11 shows an object file library sequence 350 whereas FIG. 12 shows a create a new object file sequence 400. Each sequence is accessed by interfacing with the communicator 70 as prompted by the object identification menu 225 of FIG. 7. Generally, as shown in FIG. 1, the system 15 includes a system for processing information associated with the object 50 so that the object 50 optimally receives energy from the high-energy density system 20. In one exemplary embodiment, the system for processing information includes the processor 40, the communicator 70 coupled to the processor 40, and an identifier 51 associated with the object 50. Illustratively, in one exemplary embodiment, the identifier 51 may include indicia for identifying the object by model number, associated size, and material composition thereof. As indicated by the directional arrow 72 of FIG. 1, the communicator 70 accesses the identifier 51 and generates a command signal based on the identifier 51.

In one exemplary embodiment, the system for processing information includes an object file library. The object file library contains a database in a computer readable code that interrelates information associated with the object 50 to a respective identifier 51. Accordingly, the communicator 70 scans the identifier 51 and retrieves information related to the object 50. In one exemplary embodiment, the object file library may include CAD data files. Ultimately, this information retrieved from the object file library based on the identifier 51 enables the processor 40 to configure the high-energy density system. Illustratively, for the object 50 comprising an aircraft wing as shown in FIG. 1, the communicator 70 scans the object identifier 51, such as a bar code, and accesses the object file library that is associated with the processor 40. The ultrasonic laser system thus configures the position of the laser application head 33 with respect to the robot device 30 based on physical parameters associated with the object 70 as accessed from the object file library.

In another exemplary embodiment, for system 15 lacking information from an object file library for a particular object, the processor 40 executes an object recognition sequence. The object recognition sequence and/or create a new object file sequence interface with the user via the communicator 70 so that information related to that particular object 70 is manually entered as is ultimately included within the library. Manual entry may include test scanning the object 70 to obtain physical, material, and electromagnetic parameters associated with the object 70 among other parameters. Test scanning in turn may include scanning the object 70 with the high-energy density system.

Accordingly, the system for recognizing the object includes a processor including a library. The library thus executes an object recognition sequence. The communicator coupled to the processor generates a command signal based on the object recognition sequence.

Referring to step 353, FIG. 11, for the object file library sequence 350, the user scans with the communicator 70 the object identifier 51 associated with the object 50 with the communicator 70. In step 355, the processor 40 associated with the communicator 70 retrieves an object file from the object file library for that particular object identifier 51. In step 357, the processor 40 associated with the communicator 70 interfaces with the high-energy density system 20 so that operation of the high-energy density system is based on parameters provided by the object file from the object file library.

For the create a new object file sequence 400 of FIG. 12, the communicator 70 and processor 40, in step 405, determine whether an object identifier was included with the object 50. If an object identifier is not included, the create a new object file sequence 400 assigns an identifier for the particular object in step 410 before advancing to step 415.

In one embodiment, the communicator 70 interfaces with the user to obtain desired parameters with respect to the object in step 415. Accordingly, in step 420, the processor 40 stores the parameters in memory with respect to the object identifier for the object 50. In step 425, the communicator 70 and processor 40 configure operations based on the stored parameters in step 425.

Figure 13:
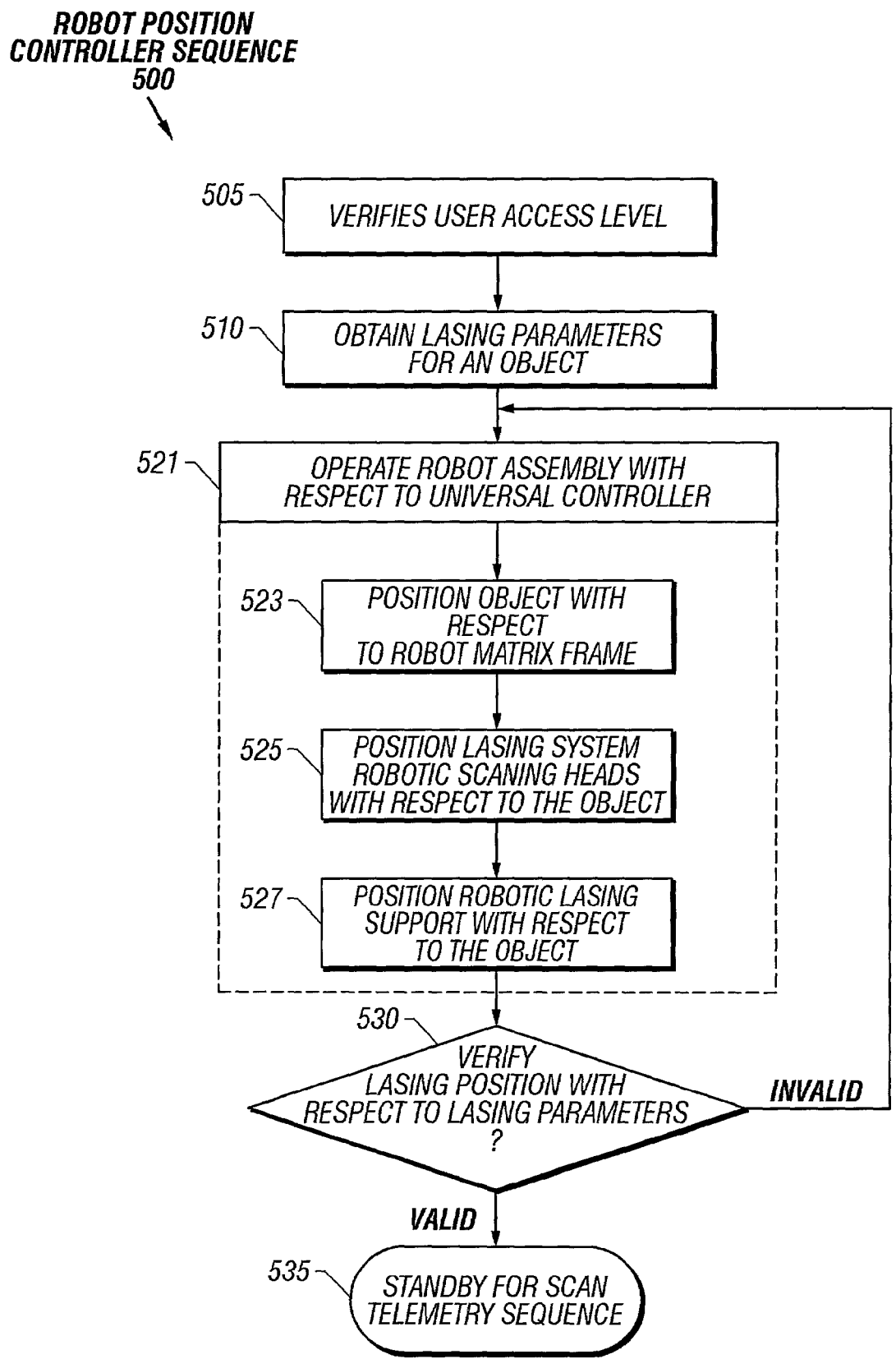
FIG. 13 is a flow diagram illustrating one embodiment of a robot position controller sequence accessed through the lasing sequence menu of FIG. 8.
Figure 14:
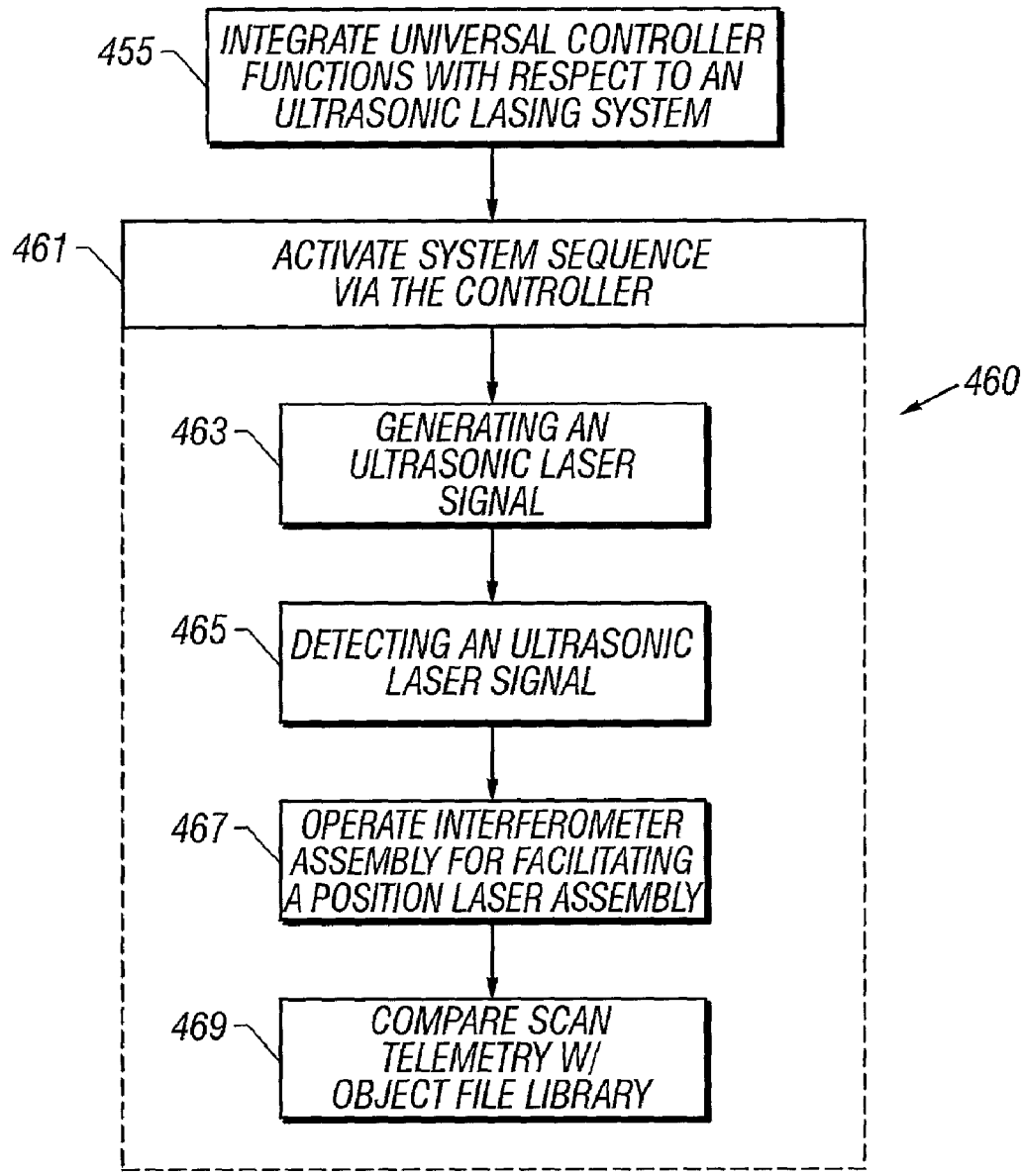
FIG. 14 is a flow diagram of one embodiment of a scan telemetry sequence accessed through the lasing sequence menu of FIG. 8.

Referring now to the scanned telemetry sequence 450 of FIG. 13 and the robot position controller sequence 500 of FIG. 14, each sequence is accessed by a user via interfacing with the lasing sequence menu 230 displayed by the communicator 70. As shown in FIG. 1, the system 15 includes a system for controlling a robotic device 30. The system for controlling a robotic device includes a processor 40 and a wireless communicator 70. As such, the communicator 70 generates a command signal. The processor 40 receives the command signal and operates the robotic device 30 based on the command signal. Ultimately, the robotic device 30 positions the laser application head 33 with respect to the object 50.

In one exemplary embodiment, the wireless communicator 70 generates at least one command signal based on a typematic rate of interface. The typematic rate of interface refers to the rate by which the communicator 70 recognizes one distinct keystroke from another. Illustratively, a typematic rate of interface will continuously display a predetermined number of characters on a computer monitor for a given period as that particular keystroke is continuously depressed. For example, by depressing a touch key for the symbol "R" for one second, a respective display associated with a communicator will indicate five "R" characters in that the typematic rate of interface is five characters displayed per second.

In one embodiment, by continuously generating at least one command signal based on the typematic rate of interface, a communicator 70 activates and thus operates the robotic device 30 based on the typematic rate of interface so long as the touch key associated with the communicator is depressed. Thus, to cease operation a user discontinues from pressing the touch key. In this manner, in terms of safety and ease of use, the robotic device and/or high-energy density system is activated only while a touch key is continuously depressed according to the typematic rate of interface.

Illustratively, referring to the robot position controller sequence 500 of FIG. 13, according to one exemplary embodiment for an ultrasonic lasing system, the wireless control of a robotic device 30 via a communicator 170 is as follows. In step 505 of FIG. 13, the communicator 70 verifies the level of user access with respect to the robotic device 30. In step 510, the communicator 70 and processor 40 obtain lasing parameters with respect to the object 70.

Generally, as shown in step 521, the communicator 70 actuates the robotic device 30 with respect to a predetermined typematic rate of interface. The user thus activates the robotic device 30 via the interface. Steps 523, 525, and 527 of the robot position controller sequence 500 show various applications, among others, for operating the robot assembly with respect to the communicator 70. In particular, in step 523, the communicator 70 positions the object by moving the gantry assembly 31. In step 525, the communicator 70 positions the laser application head 33 via the robotic device 30 with respect to the object 50. In step 527, with the communicator 70, the robotic device 30 positions the high-energy density system with respect to the object 50.

In step 530, the controller 70 and processor 40 verify whether the position achieved by controlling the robotic device 30. In particular, the processor 40 determines whether the communicator 70 is within the parameters initially specified by the user. If the desired parameters have not yet been achieved, the robot position controller sequence 500 will continue via step 521. However, if the desired parameters are obtained, the robot position controller sequence 500 advances from step 530 to step 535. In step 535, the communicator 70 and processor 40 ensure that the system 15 is on stand-by to commence operations of the high-energy density system 20.

Illustratively, FIG. 14 shows a scan telemetry sequence 450 for a high-energy density system comprising an ultrasonic lasing system. In general, the communicator 70 is used to activate the automated sequence for scanning an object so as to gather information regarding the physical parameters of that object including material and structural attributes among others.

Accordingly, in step 455, a communicator 70 is operationally coupled with an ultrasonic lasing system. In general, for step 460, the scanned telemetry sequence 450 implements an automated operation sequence via the communicator 70. Thus, in step 461, the automated operation sequence for the ultrasonic lasing system is activated by interfacing with the communicator 70.

In step 463, the ultrasonic laser assembly generates an ultrasonic laser signal. In step 465, the ultrasonic laser signal is reflected off of the object 50 is detected by the ultrasonic lasing system. In step 467, the automated operation sequence 460 includes a feedback system for optimizing generation and receipt of an ultrasonic laser signal.

In step 469, the system 15 compares the scanned telemetry based on the received ultrasonic laser signal with an object file from the object file library. Thus, the system 15 in one exemplary embodiment may inspect an object by comparing telemetry based on the received ultrasonic laser signal with ideal parameters for that related object.

Although the present invention has been described in detail, it should be understood that various changes, substitutions, and alterations could be made hereto without departing from the spirit and scope of the invention as defined by the appended claims.

What is claimed is:

1. A wireless system operable to issue commands to a robotic device according to a typematic rate of interface, the system including:
   a processor operably coupled to the robotic device, wherein the robotic device further comprises a laser ultrasonic non destructive evaluation (NDE) inspection system operable to generate and detect ultrasonic surface displacements on a remote object;
   the laser ultrasonic system linked with the processor; and
   a wireless communicator operably interfaced to the processor wherein the wireless communicator is operable to generate at least one command signal based on the typematic rate of interface;
   the processor is operable to issue the at least one command signal to the robotic device wherein the processor is operable to issue a second command signal when the typematic rate of interface changes beyond a predetermined threshold.

2. The wireless system of claim 1 further including a restricted system.

3. The wireless system of claim 2 wherein the restricted system includes a barrier.

4. The wireless system of claim 3 wherein the lasing system is enclosed by the barrier.

5. The wireless system of claim 3 wherein the wireless communicator opens the barrier.

6. The wireless system of claim 1 wherein the lasing operations include controlling a robotic device.

7. The wireless system of claim 6 wherein the wireless communicator generates a command signal associated with the robotic device.

8. The wireless system of claim 6 wherein the wireless communicator generates a command signal based on the typematic rate of interface.

9. The wireless system of claim 6 wherein the wireless communicator continuously generates a command signal based on a typematic rate of interface.

10. The wireless system of claim 6 wherein the wireless communicator continuously generates a plurality of command signals based on the typematic rate of interface.

11. A wireless controller operable to issue commands to a robotic device according to a typematic rate of interface, the wireless controller comprising:
    a processor operably coupled to the robotic device, wherein the robotic device further comprises a high-energy density system;
    a wireless communicator operably coupled to the processor wherein the wireless communicator is operable to generate at least one command signal based on the typematic rate of interface;
    the processor is operable to issue the at least one command signal to the robotic device wherein the processor is operable to issue a second command signal when the typematic rate of interface changes beyond a predetermined threshold.

12. A wireless controller operable to issue commands to a robotic device according to a typematic rate of interface, the system comprising:
    a processor operably coupled to the robotic device, wherein the robotic device further comprises a laser ultrasonic system operable to generate and detect ultrasonic surface displacements on a remote object; and
    a wireless communicator operably interfaced to the processor wherein the wireless communicator is operable to generate at least one command signal based on the typematic rate of interface; and
    the processor is operable to issue the at least one command signal to the robotic device wherein the processor is operable to issue a second command signal when the typematic rate of interface changes beyond a predetermined threshold.

13. A controller operable to issue to an emergency stop command according to a typematic rate of interface, the controller comprising:
    a processor operably coupled to the high-energy density system;
    a wireless communicator operably coupled to the processor wherein the wireless communicator is operable to generate at least one command signal based on the typematic rate of interface;
    the processor is operable to issue the at least one command signal to the high-energy density system wherein the processor is operable to issue the emergency stop command signal when the typematic rate of interface changes beyond a predetermined threshold.

* * * * *